US006812004B1

(12) United States Patent
Caux et al.

(10) Patent No.: US 6,812,004 B1
(45) Date of Patent: Nov. 2, 2004

(54) MAMMALIAN DENDRITIC CELL CHEMOKINE REAGENTS

(75) Inventors: Christophe Caux, Lyons (FR); Serge J. E. Lebecque, Civrieux d'Azergue (FR); Jacques Banchereau, Dallas, TX (US)

(73) Assignee: Schering Corporation, Kenilworth, NJ (US)

(*) Notice: Subject to any disclaimer, the term of this patent is extended or adjusted under 35 U.S.C. 154(b) by 639 days.

(21) Appl. No.: 08/799,028

(22) Filed: Feb. 10, 1997

Related U.S. Application Data

(60) Provisional application No. 60/012,108, filed on Feb. 12, 1996.

(51) Int. Cl.[7] .......................... C12N 15/19; C12N 1/21; C12N 5/10; C12N 15/63; C07K 14/52
(52) U.S. Cl. .................. 435/69.5; 435/243; 435/320.1; 435/71.1; 435/325; 530/351; 536/23.5
(58) Field of Search ............................... 435/69.5, 71.1, 435/243, 325, 320.1, 69.1, 520.1, 252.3; 536/23.5; 530/351; 514/44

(56) References Cited

FOREIGN PATENT DOCUMENTS

| WO | WO97/07198 | 2/1997 |
|----|------------|--------|
| WO | WO97/11969 | 4/1997 |

OTHER PUBLICATIONS

Sara et al., IDC 271 (35) Aug. 1996, p. 21514.*
Imai et al Genbank Submission 1994, Accession No D43767.*
Adena et al, Nature 387, 1997, p. 713.*
Hishoma et al, J. Immonul 159, 1997, p. 1140 (abst only).*
Vicuri et al, Immunity 7(2) 1997, p. 271 (abst only).*
Zlstnik J. Immunol 157, 1996 p. 2726.*
Warren et al, 9th International Cong. Immunol, 1995, #109.*
Derwent Geneseq Patent Sequence Database, Accession No. 97P–W22889, citing: WO 9729192 A1, date Aug. 14, 1997; WO97–US1248, date Feb. 7, 1997; US 96–600114, date Feb. 12, 1996. "Search record pertaining to human Dendrokine, performed on Jul. 7, 1998".
Derwent Geneseq Patent Sequence Database, Accession No. 97P–W14917, citing: WO9711969 A1, date Apr. 3, 1997; WO 96–JP2801, date Sep. 27 1996; JP 96–56044, date Mar. 13, 1996; JP 95–249457, date Sep. 27, 1995. "Search record pertaining to human Dendrokine, performed on Jul. 7, 1998".
Derwent Geneseq Patent Sequence Database, Accession No. 97P–W14918, citing: WO 9711969 A1, date Apr. 3, 1997; WO 96–JP2801, date Sep. 27, 1996; JP 96–56044, date Mar. 13, 1996; JP 95–249457, date Sep. 27, 1995. "Search record pertaining to human Dendrokine, performed on Jul. 7, 1998".
Derwent Geneseq Patent Sequence Database, Accession No. 97P–W38171, citing: WO 9741230 A1, date Nov. 6, 1997; WO 97–EP2217, date Apr. 30, 1997; DE 96–19617312, date Apr. 30, 1996. "Search record pertaining to human Dendrokine, performed on Jul. 7, 1998".
Derwent Geneseq Patent Sequence Database, Accession No. 96P–R95691, citing: WO 9616979 A1, date Jun. 6, 1996: WO 95–US15484, date Nov. 29, 1995: US 94–347492, date Sep. 27, 1995. "Search record pertaining to human Dendrokine, performed on Jul. 7, 1998".
Zhugong Liu, et al., Chem. Abstracts, 121(19):869, Abstr. 228443z, 1994. "Cytokine production by MTSC 4 cells, an established mouse thymic dendritic cell line".
Mansour Mohamadzadeh, et al., Journal of Immunology, 156:3102–3106, 1996. "Dendritic Cells Produce Macrophage Inflamatory Protein–1γ, a New Member of the CC Chemokine Family".
Toshio Imai, et al., J. of Biological Chemistry, 271(35):21514–21521, 1996. "Molecular Cloning of a Novel T Cell–directed CC Chemokine Expressed in Thymus by Signal Sequence Trap Using Epstein–Barr Virus Vector".
Kevin B. Bacon, et al., Int. Arch. Allergy Immunol., 109:97–109, 1996. "Chemokines as Mediators of Allergic Inflammation".
Michael J. Berridge, Nature 361:315–325, Jan. 28, 1993. "Inositol triphosphate and calcium signaling".
M. Motasim Billah, et al., Biochem. J., 269:281–291, 1990. "The regulation and cellular functions of phosphatidylecholine hydrolysis".
Marcus W. Bosenberg, et al., Cell, 71:1157–1165, Dec. 24, 1992. "The Cytoplasmic Carboxy–Terminal Amino Acid Specifies Cleavage of MembraneTGF α into Soluble Growth Factor".
Fiorenza Cocchi, et al., Science, 270:1811–1815, Dec. 15, 1995. "Identification of Rantes, MIP–1α, and MIP–1β as the Major HIV–Suppressive Factors Produced by CD8+ T Cells".
Angela M. Gronenborn, et al., Prot. Engineering.. 4(33):263–269, 1991. "Modeling the three–dimensional structure of the monocyte chemo–attractant and activating protien MCAF/MCP–1 on the basis of the solution structure of interleukin–8".
Gregory S. Kelner, et al., Science, 266:1395–1399, Nov. 25, 1994. "Lymphotactin: A Cytokine That Represents a New Class of Chemokine".

(List continued on next page.)

Primary Examiner—Christine J. Saoud
(74) Attorney, Agent, or Firm—Michael G. Biro; Immac J. Thampoe

(57) ABSTRACT

A novel CC chemokine which is from a mammal, reagents related thereto including purified proteins, specific antibodies, and nucleic acids encoding said chemokine. Methods of using said reagents and diagnostic kits are also provided.

9 Claims, No Drawings

OTHER PUBLICATIONS

Patricia J. Lodi, et al., *Science*, 263: 1762–1767, Mar. 25, 1994. "High–Resolution Solution Structure of the β Chemokine hMIP–1β by Multidimensional NMR".

Lina Lu, et al., *Transplantation*, 60(12):1539–1545, Dec. 27, 1995. "Bone Marrow–Derived Dendritic Cell Progenitors (NLDC 145+, MHC Class II+, B7–2–) Induce Alloantigen–Specific Hyporesponsiveness in Murine T Lymphocytes".

Kouji Matsushima, et al., *Cytokine*, 1:2–13, Nov. 1989. "Interleukin 8 and MCAF: Novel Inflammatory Cytokines Inducible by IL 1 and TNF".

Michael D. Miller, et al., *Crit. Rev. Immunol.*, 12:17–46, 1992. "Biology and Biochemistry of the Chemokines: A Family of Chemotatic and Inflammatory Cytokines".

Michael D. Miller, et al., *Proc. Nat'l. Acad. Sci.*, 89:2950–2954, Apr. 1992. "The Human Cytokine I–309 is a Monocyte Chemoattractant".

Joost J. Oppenheim, et al., *Ann. Rev. Immunol.*, 9:617–648, 1991. "Properties of The Novel Proinflammatory Supergene 'Intercrine' Cytokine Family".

Atanasio Pandiella, et al., *J. Biol. Chem.*, 267:24028–24033, 1992. "Cleavage of Membrane–archored Growth Factors Involes Distinct Protease Activities Regulated through Common Mechanisms".

Lesya M. Pinchuk, et al., *Immunity*, 1:317–325, Jul. 1994. "The Role of CD40 and CD80 Accessory Cell Molecules in Dendritic Cell–Dependent HIV–1 Infection".

Melissa Pope, et al., *J. Exp. Med.*, 182:2045–2056, Dec. 1995. "Low Levels of HIV–1 Infection in Cutaneous Dendritic Cells Promote Extensive Viral Replication upon Binding to Memory CD4+ T Cells".

M. Pope, et al., *Cell*, 78:389–396, Aug. 12, 1994. "Conjugates of Dendritic Cells and Memory T Lymphocytes from Skin Facilitate Productive Infection with HIV–1".

Thomas J. Schall, et al., *Curr. Opin. Immunol.*, 6:865–873, 1994. "Chemokines, leukocyte trafficking, and inflammation".

Thomas J. Schall in *The Cytokine Handbook*, 2nd ed., Academic Press Ltd., 1994, chapter 22, pp 419–323, "The Chemokines".

Thomas J. Schall, *Cytokine* 3:165–183, May 1991. "Biology of the Rantes/sis Cytokine Family".

Thomas E. Starzl, et al., *The Lancet*, 399:1579–1582, Jun 27, 1992. "Cell migration, chimerism, and graft acceptance".

Ralph Steinman, *Ann Rev. Immunol.*, 9:271–296, 1991. "The DendriticCell System and Its Role in Immunogenicity".

Mark Y. Stoeckle, et al., *The New Biologist*, 2:313–323, Apr. 1990. "Two Burgeoning Families of Platelet Factor 4–Related Proteins: Mediators of the Inflammatory Response".

Jacques Banchereau, et al.(eds.), *Dendritic Cells in Fundamental and Clinical Immunology*, vol. 2, Plenum Press, NY, title page and table of contents, 1995.

Jacques Banchereau, et al.(eds.), *Dendritic Cells in Fundamental and Clinical Immunology*, vol. 2, Plenum Press, NY, pp. 1–5, 1995.

Jacques Banchereau, et al.(eds.), *Dendritic Cells in Fundamental and Clinical Immunology*, vol. 2, Plenum Press, NY, pp. 17–20, 1995.

Jacques Banchereau, et al.(eds.), *Dendritic Cells in Fundamental and Clinical Immunology*, vol. 2, Plenum Press, NY, pp. 43–52, 1995.

Jacques Banchereau, et al.(eds.), *Dendritic Cells in Fundamental and Clinical Immunology*, vol. 2, Plenum Press, pp. 71–73, 1995.

\* cited by examiner

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 333 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..330

(ix) FEATURE:
      (A) NAME/KEY: sig_peptide
      (B) LOCATION: 49..117

(xi) SEQUENCE DESCRIPTION: SEQ ID NO:1:

```
CTG AGC AGA GGG ACC TGC ACA GAG ACT CCC TCC TGG GCT CCT GGC ACC      48
Leu Ser Arg Gly Thr Cys Thr Glu Thr Pro Ser Trp Ala Pro Gly Thr
 1               5                  10                  15

ATG GCC CCA CTG AAG ATG CTG GCC CTG GTC ACC CTC CTC CTG GGG GCT      96
Met Ala Pro Leu Lys Met Leu Ala Leu Val Thr Leu Leu Leu Gly Ala
            20                  25                  30

TCT CTG CAG CAC ATC CAC GCA GCT CGA GGG ACC AAT GTG GGC CGG GAG     144
Ser Leu Gln His Ile His Ala Ala Arg Gly Thr Asn Val Gly Arg Glu
        35                  40                  45

TGC TGC CTG GAG TAC TTC AAG GGA GCC ATT CCC CTT AGA AAG CTG AAG     192
Cys Cys Leu Glu Tyr Phe Lys Gly Ala Ile Pro Leu Arg Lys Leu Lys
    50                  55                  60

ACG TGG TAC CAG ACA TCT GAG GAC TGC TCC AGG GAT GCC ATC GTT TTT     240
Thr Trp Tyr Gln Thr Ser Glu Asp Cys Ser Arg Asp Ala Ile Val Phe
65                  70                  75                  80

GTA ACT GTG CAG GGC AGG GCC ATC TGT TCG GAC CCC AAC AAC AAG AGA     288
Val Thr Val Gln Gly Arg Ala Ile Cys Ser Asp Pro Asn Asn Lys Arg
                85                  90                  95

GTG AAG AAT GCA GTT AAA TAC CTG CAA AGC CTT GAG AGG TCT             330
Val Lys Asn Ala Val Lys Tyr Leu Gln Ser Leu Glu Arg Ser
            100                 105                 110

TGA                                                                  333
```

(2) INFORMATION FOR SEQ ID NO:2:

(i) SEQUENCE CHARACTERISTICS:
      (A) LENGTH: 110 amino acids
      (B) TYPE: amino acid
      (D) TOPOLOGY: linear (ii) MOLECULE TYPE: protein (xi) SEQUENCE DESCRIPTION: SEQ ID NO:2:

```
Leu Ser Arg Gly Thr Cys Thr Glu Thr Pro Ser Trp Ala Pro Gly Thr
 1               5                  10                  15

Met Ala Pro Leu Lys Met Leu Ala Leu Val Thr Leu Leu Leu Gly Ala
            20                  25                  30

Ser Leu Gln His Ile His Ala Ala Arg Gly Thr Asn Val Gly Arg Glu
        35                  40                  45
```

-continued

```
Cys Cys Leu Glu Tyr Phe Lys Gly Ala Ile Pro Leu Arg Lys Leu Lys
    50              55              60

Thr Trp Tyr Gln Thr Ser Glu Asp Cys Ser Arg Asp Ala Ile Val Phe
65              70              75              80

Val Thr Val Gln Gly Arg Ala Ile Cys Ser Asp Pro Asn Asn Lys Arg
            85              90              95

Val Lys Asn Ala Val Lys Tyr Leu Gln Ser Leu Glu Arg Ser
            100             105             110
```

US 6,812,004 B1

MAMMALIAN DENDRITIC CELL CHEMOKINE REAGENTS

The present filing is a conversion to a regular U.S. Patent Application of a U.S. Provisional Patent Application 60/012,108, filed Feb. 12, 1996, which is incorporated herein by reference.

FIELD OF THE INVENTION

The present invention is directed to compositions related to proteins which function in controlling development and differentiation of mammalian cells, e.g., cells of a mammalian immune system. In particular, it provides proteins and mimetics, and antibodies which regulate development, differentiation, and function of various cell types, including hematopoietic cells.

BACKGROUND OF THE INVENTION

The circulating component of the mammalian circulatory system comprises various cell types, including red and white blood cells of the myeloid, lymphoid, megakaryotoid, or the erythroid cell lineages. See, e.g., Rapaport (1987) *Introduction to Hematology* (2d ed.) Lippincott, Philadelphia, Pa.; Jandl (1987) *Blood: Textbook of Hematology*, Little, Brown and Co., Boston, Mass.; and Paul (ed. 1993) *Fundamental Immunology* 3d ed., Raven Press, N.Y. Progression through various stages of differentiation are regulated by various signals provided to the cells, often mediated through a class of soluble proteins known as the cytokines. Within this class of molecules is a group known as the chemoattractant cytokines, or chemokines. See, e.g., Schall (1994) "The Chemokines" in *The Cytokine Handbook* (2d ed.) Academic Press; Schall and Bacon (1994) *Current Opinion in Immunology* 6:865–873.

Although the chemokines have not been tested over the full spectrum of biological activities, the best described biological functions of these molecules relate to chemoattraction of leukocytes. However, new chemokine-like molecules are being discovered, and their biological effects on the various cells responsible for immunological responses are topics of continued study.

Many observations indicate that other factors exist whose functions in hematopoiesis, immune development, and leukocyte trafficking are heretofore unrecognized. These factors provide possible biological activities whose spectra of effects are distinct from known differentiation, activation, or other signaling factors. Moreover, new biological activities of chemokine-like molecules on other cell types have yet to be discovered. The absence of knowledge about the structural, biological, and physiological properties of the regulatory factors which regulate, e.g., hematopoietic cell physiology in vivo, prevents the modification of the effects of such factors. Thus, medical conditions where regulation of the development or physiology of relevant cells is required remain unmanageable.

SUMMARY OF THE INVENTION

The present invention is based, in part, upon the discovery of new genes, designated dendrokines, encoding members of the class of CC chemokines. These dendrokines appear to be specifically expressed in dendritic cells. It embraces agonists and antagonists of the dendrokines, e.g., mutations (muteins) of the natural sequences, fusion proteins, chemical mimetics, antibodies, and other structural or functional analogs. It is also directed to isolated genes encoding proteins of the invention. Various uses of these different protein or nucleic acid compositions are also provided.

The present invention provides a substantially pure dendrokine; a fusion protein comprising dendrokine sequence; an antibody or antigen binding fragment thereof which exhibits specificity of binding to a dendrokine; and a nucleic acid encoding a dendrokine or fusion protein thereof.

In dendrokine embodiments, the chemokine may comprise a mature dendrokine sequence of Table 1; have a natural sequence; exhibit a post-translational modification pattern distinct from natural dendrokine; be 3-fold or fewer substituted from a natural sequence; be detectably labeled; be attached to a solid substrate; or be denatured. The invention also embraces a sterile composition comprising the dendrokine. The dendrokine composition may also attract a cell of hematopoietic origin.

In fusion protein embodiments, the protein may comprise either sequence of Table 1; and/or sequence of another cytokine or chemokine.

In antibody embodiments, the dendrokine can be a human protein or denatured; or the antibody may be raised against a peptide sequence of Table 1 or a purified primate dendrokine; may be a monoclonal antibody; be from a rabbit or mouse; be detectably labeled; be attached to a solid substrate; or bind to said dendrokine with a Kd of at least about 300 $\mu$M. Binding fragments of the antibodies can be an Fv fragment, an Fab fragment, or an F(ab)2 fragment; be fused to another protein segment; or be coupled to another chemical moiety.

The invention further provides methods of making a dendrokine-antibody complex by contacting a primate dendrokine to a binding antibody; and may further allow purification of the dendrokine or antibody.

In nucleic acid embodiments, the chemokine may be from a primate, including a human, or have a naturally occurring sequence. The nucleic acid may have a natural sequence; hybridize at 65° C. and 50 mM salt to the coding sequence of Table 1; comprise a coding sequence of Table 1; be detectably labeled; be an expression vector; be operably associated with a regulatory or control sequence; be at least about 330 nucleotides in length; be a PCR product, or comprise a deoxyribonucleic acid nucleotide. The invention also provides a method of making a chemokine protein comprising a step of expressing such a nucleic acid.

The invention also provides a kit comprising: a substantially pure dendrokine, or fragment thereof; an antibody which binds with specificity to a mammalian dendrokine; or a nucleic acid encoding a dendrokine or peptide of about 17 amino acids. The kit may also be capable of making a qualitative or quantitative analysis.

In another embodiment, the invention provides methods of modulating physiology or development of a cell comprising contacting the cell with an agonist or antagonist of a mammalian dendrokine. The antagonist may be an antibody against a mammalian dendrokine and result in the regulation of autoimmunity, tissue rejection, or an undesired response to an antigen. In embodiments encompassing an agonist, the modulating can result in the regulation of an infectious disease, a vaccine response, or a cancer.

DETAILED DESCRIPTION OF THE PREFERRED EMBODIMENTS

OUTLINE
I. General
II. Purified Chemokine
   A. physical properties
   B. biological properties
III. Physical Variants
   A. sequence variants, fragments
   B. post-translational variants
      1. glycosylation
      2. others
IV. Functional Variants
   A. analogs; fragments
      1. agonists
      2. antagonists
   B. mimetics
      1. protein
      2. chemicals
   C. species variants
V. Antibodies
   A. polyclonal
   B. monoclonal
   C. fragments, binding compositions
VI. Nucleic Acids
   A. natural isolates; methods
   B. synthetic genes
   C. methods to isolate
VII. Making Chemokine; Mimetics
   A. recombinant methods
   B. synthetic methods
   C. natural purification
VIII. Uses
   A. diagnostic
   B. therapeutic
IX. Kits
   A. nucleic acid reagents
   B. protein reagents
   C. antibody reagents I. General The present invention provides DNA sequences encoding various mammalian proteins which exhibit structural properties characteristic of a chemotactic cytokine, or chemokine. See, e.g., Lodi, et al. (1994) *Science* 263:1762–1767; Gronenborn and Clore (1991) *Protein Engineering* 4:263–269; Miller and Kranger (1992) *Proc. Nat'l Acad. Sci. USA* 89:2950–2954; Matsushima and Oppenheim (1989) *Cytokine* 1:2–13; Stoeckle and Baker (1990) *New Biol.* 2:313–323; Oppenheim, et al. (1991) *Ann. Rev. Immunol.* 9:617–648; Schall (1991) Cytokine 3:165–183; and *The Cytokine Handbook* Academic Press, N.Y. Human embodiments are provided.

Chemokines which have been tested play an important role in immune and inflammatory responses by inducing migration and adhesion of leukocytes. These small secreted molecules are a growing superfamily of 8–14 kDa proteins originally characterized by a conserved four cysteine motif. See, e.g., Schall. (1991) *Cytokine* 3:165–183; and *The Cytokine Handbook* Academic Press, N.Y. Classically, the chemokines are secreted by activated leukocytes and act as a chemoattractant for a variety of cells which are involved in inflammation. Besides chemoattractant properties, chemokines have been shown to induce other biological responses, e.g., modulation of second messenger levels such as $Ca^{++}$; inositol phosphate pool changes, see, e.g., Berridge (1993) *Nature* 361:315–325, or Billah and Anthes (1990) *Biochem. J.* 269:281–291; cellular morphology modification responses; phosphoinositide lipid turnover; possible antiviral responses; enhancing or suppressing effects on the proliferation of myeloid progenitor cells; and others. Likewise, dendrokines may, alone or in combination with other therapeutic reagents, have similar advantageous combination effects. Since dendritic cells are known to initiate immune responses via a role in antigen presentation, chemoattractant functions are suggested. These would include, e.g., attraction or activation of effector cells, e.g., T cells and/or B cells, or other cell types, e.g., eosinophils, basophils, monocytes, macrophages, dendritic cells, and/or neutrophils. The dendrokines may also have chemoattractive effects on various neural cells including, e.g., dorsal root ganglia neurons in the peripheral nervous system and/or central nervous system neurons.

The chemokine superfamily was originally divided into two main groups exhibiting characteristic structural motifs, the Cys-X-Cys (C-X-C) and Cys-Cys (C-C) families. These are distinguished on the basis of a single amino acid insertion between the NH-proximal pair of cysteine residues and sequence similarity. Typically, the C-X-C chemokines, e.g., IL-8 and MGSA/Gro-α, act on neutrophils but not on monocytes, whereas the C-C chemokines, e.g., MIP-1α and RANTES, are potent chemoattractants for monocytes and lymphocytes but not neutrophils. See, e.g., Miller, et al. (1992) *Crit. Rev. Immunol.* 12:17–46. A recently isolated chemokine, lymphotactin, does not belong to either group and may constitute a first member of a third chemokine family, the C family. Lymphotactin does not have a characteristic CC or CXC motif, and acts on lymphocytes but not neutrophils and monocytes. See, e.g., Kelner et al. (1994) *Science* 266:1395–1399; Schall (1994) "The Chemokines" in *The Cytokine Handbook* (2d ed.) Academic Press; and Schall and Bacon (1994) *Current Opinion in Immunology* 6:865–873.

The dendrokine molecules described herein are members of the C-C chemokine family and are so named because of their specific expression in dendritic cells. Based, in part, upon the general chemoattractant properties of chemokines, the dendrokines may attract hematopoietic cells including, e.g., accessory T and B cells, myeloid cells, eosinophils, basophils, monocytes and/or macrophages.

Dendritic cells are antigen presenting cells (APCs) that function to initiate several immune responses such as the sensitization of MHC-restricted T cells, the rejection of organ transplants, and the formation of T cell-dependent antibodies. See, e.g., Paul *Fundamental Immunology*. Dendritic cells are found in many non-lymphoid tissues but can migrate via the afferent lymph or the blood stream, e.g., to the T cell-dependent areas of lymphoid organs. They are found in the skin, where they are known as Langerhans cells, and are also present in the mucosa. Antigen presentation also is performed by interdigitating follicular cells. The APC represent the sentinels of the immune system within the peripheral tissues where they can capture antigens.

Dendritic cells are motile, and efficiently cluster and activate T cells that are specific for stimuli on the cell surface. High levels of MHC class-I and -II products and several adhesins, i.e., ICAM-1 and LFA-3, as well as co-stimulatory molecules, i.e., B7-1, B7-2, and CD40, are likely to contribute to these functions. As immature cells, dendritic cells are scattered throughout the body in non-lymphoid organs where they capture and process antigen. Subsequently, these cells move to the T-dependent areas of the secondary lymphoid organs where they present their antigen to resting T cells. Dendritic cells are specialized to mediate several physiologic components of immunogenicity, e.g., the acquisition of antigens in tissues, the migration to lymphoid organs, and the selection and activation of antigen-specific T cells.

Because of the antigen presenting function of dendritic cells, a chemokine attracting cells of hematopoietic origin to dendritic cells will permit the launching and development of effector immune responses. Thus, administering such molecules will be useful in the treatment of various disease conditions, e.g., characterized by reduced immunity. The capacity to initiate or improve immune responses make chemokines produced by dendritic cells attractive candidates to fight both infectious diseases and cancers, or as a vaccine adjuvant for an immunocompromised individual. In contrast, an antagonist to a dendritic cell chemokine may be valuable in preventing and/or regulating autoimmunity, tissue rejection, or an undesired immune response to exposure to an antigen, e.g., as observed in hematopoietic conditions such as atopy, asthma, etc. Recently, a direct effect of chemokines on retroviral infections, e.g., HIV, has been reported. See Cocchi, et al. (1995) *Science* 270:1811–1815. A role for a dendritic cell chemokine in this process can be envisaged, e.g., since the HIV replication is explosive in dendritic cell-T cell conjugates. See Pope, et al. (1994) *Cell* 78:389–398; Pope, et al. (1995) *J. Ex. Med.* 182:2045–2056; and Pinchuk, et al. (1994) *Immunity* 1:317–32.

The factors that stimulate and direct the movement of hematopoietic cells to dendritic cells in vivo have yet to be elucidated. The described chemokine should be important for understanding this motility as well as mediating various aspects of cellular physiology or development involving dendritic cells.

II. Purified Dendrokine

Nucleotide and amino acid sequences of a human chemokine are provided in Table 1. The human nucleotide sequences correspond to SEQ ID NO: 1 and amino acid sequences correspond to SEQ ID NO: 2. The amino acid sequence, provided amino to carboxy, is important in providing sequence information on the ligand allowing for distinguishing the protein from other proteins. Moreover, the peptide sequences allow preparation of peptides to generate antibodies to recognize such segments. Nucleic acid sequences allow preparation of oligonucleotide probes, useful for isolation of, e.g., cloning or identification of genes encoding such sequences. Similarities have been observed with other cytokines. See, e.g., Bosenberg, et al. (1992) *Cell* 71:1157–1165; Huang, et al. (1992) *Molecular Biology of the Cell* 3:349–362; and Pandiella, et al. (1992) *J. Biol. Chem,* 267:24028–24033.

Table 1: Nucleotide sequence (5'to 3') of human dendrokine and the corresponding amino acid sequence (amino to carboxy), SEQ ID NO: 1 and 2. The presumptive coding region runs from nucleotide 49 to 333 (end of termination codon). The conserved four cysteine residues are indicated by asterisks underneath. A predicted signal sequence is underlined, thus a mature protein would likely extend from ala to ser.

```
dendrokine (SH046 clone)
             10           20           30           40           50
     *    *     *    *     *    *     *    *     *    *     *
CTG AGC AGA GGG ACC TGC ACA GAG ACT CCC TCC TGG GCT CCT GGC ACC ATG
Leu Ser Arg Gly Thr Cys Thr Glu Thr Pro Ser Trp Ala Pro Gly Thr Met>

60           70           80           90          100
     *    *     *    *     *    *     *    *     *    *     *
GCC CCA CTG AAG ATG CTG GCC CTG GTC ACC CTC CTC CTG GGG GCT TCT CTG
Ala Pro Leu Lys Met Leu Ala Leu Val Thr Leu Leu Leu Gly Ala Ser Leu>

110          120          130          140          150
     *    *     *    *     *    *     *    *     *    *     *
CAG CAC ATC CAC GCA GCT CGA GGG ACC AAT GTG GGC CGG GAG TGC TGC CTG
Gln His Ile His Ala Ala Arg Gly Thr Asn Val Gly Arg Glu Cys Cys Leu>
                                                         *   *

160          170          180          190          200
     *    *     *    *     *    *     *    *     *    *
GAG TAC TTC AAG GGA GCC ATT CCC CTT AGA AAG CTG AAG ACG TGG TAC CAG
Glu Tyr Phe Lys Gly Ala Ile Pro Leu Arg Lys Leu Lys Thr Trp Tyr Gln>

210          220          230          240          250
     *    *     *    *     *    *     *    *     *    *     *
ACA TCT GAG GAC TGC TCC AGG GAT GCC ATC GTT TTT GTA ACT GTG CAG GGG
Thr Ser Glu Asp Cys Ser Arg Asp Ala Ile Val Phe Val Thr Val Gln Gly>
                     *

260          270          280          290          300
     *    *     *    *     *    *     *    *     *    *     *
AGG GCC ATC TGT TCG GAC CCC AAC AAC AAG AGA GTG AAG AAT GCA GTT AAA
Arg Ala Ile Cys Ser Asp Pro Asn Asn Lys Arg Val Lys Asn Ala Val Lys>
             *

310          320          330
     *    *     *    *     *
TAC CTG CAA AGC CTT GAG AGG TCT TGA
Tyr Leu gln Ser Leu Glu Arg Ser ***>
```

Comparison between the chemokine and other chemokine family members can be performed. See, e.g., Lodi, et al (1994) *Science* 263:1762–1766. In particular, β-sheet and α-helix residues can be determined using, e.g., RASMOL program, see Sayle and Milner-White (1995) *TIBS* 20:374–376; or Gronenberg, et al. (1991) *Protein Engineering* 4:263–269; and other structural features defined in Lodi, et al. (1994) *Science* 263:1762–1767.

Based upon the structural modeling and insights in the binding regions of the chemokines, it is predicted that residues in the mature protein, lacking a signal of about 23 residues, 19 (ile), 20 (pro), 27 (trp), 28 (tyr), 29 (gln), 39 (ile), 40 (val), 42 (val), 47 (arg), and 53 (pro) are likely to be important for chemokine binding to cells. Residues at the amino terminus are probably not involved in receptor binding or specificity.

As used herein, the term "dendrokine" shall encompass, when used in a protein context, a protein having human amino acid sequences shown in Table 1. The invention also embraces a polypeptide comprising a significant fragment of such proteins, as well as to a human derived polypeptide which exhibits equivalent biological function or interacts with dendrokine specific binding components. These binding components, e.g., antibodies, typically bind to a dendrokine with high affinity, e.g., at least about 100 nM, usually better than about 30 nM, preferably better than about 10 nM, and more preferably at better than about 3 nM. Homologous proteins would be found in mammalian species other than humans, e.g., monkeys, and will likely include rodent proteins, e.g., mice and rats. Non-mammalian species should also possess structurally or functionally related genes and proteins.

The term "polypeptide" as used herein includes a significant fragment or segment, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids, e.g., about 35, 40, 45, 50, 60, 75, 80, 100, 120, etc. such peptides may begin at positions other than the natural amino terminus, e.g., positions 1, 2, 5, 10, 20, etc., and may end at other than the natural carboxy terminus, e.g., 85, 84, etc.

The term "binding composition" refers to molecules that bind with specificity to dendrokine, e.g., in a ligand-receptor type fashion or, preferably, an antibody-antigen interaction. Various compounds, e.g., proteins, may also specifically associate with dendrokine, including natural physiologically relevant protein-protein interactions, either covalent or non-covalent. No implication as to whether the dendrokine presents a concave or convex shape in its ligand-receptor interaction is intended, other than the interaction exhibit high binding specificity, e.g., specific affinity. A functional analog may be a ligand with structural modifications, or may be a wholly unrelated molecule, e.g., which has a molecular shape which interacts with the appropriate ligand binding determinants. The ligands may serve as agonists or antagonists of the receptor, see, e.g., Goodman, et al. (eds.) (1990) *Goodman & Gilman's: The Pharmacological Bases of Therapeutics* (8th ed.), Pergamon Press.

Substantially pure means that the protein is free from other contaminating proteins, nucleic acids, and/or other biologicals typically derived from the original source organism. Purity may be assayed by standard methods, and will ordinarily be at least about 40% pure, more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, and in most preferred embodiments, at least 99% pure. Purity may be based on molar or weight ratios.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength, where advantageous. The actual ions may be modified, e.g., to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS (cholesteryl hemisuccinate) or CHAPS (3-[3-cholamidopropyl dimethlyammonio]-1-propane sulfonate), or a low enough concentration as to avoid significant disruption of structural or physiological properties of the ligand.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman; and Cantor and Schimmel (1980) *Biophysical Chemistry*, parts 1–3, W. H. Freeman & Co., San Francisco. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S.

III. Physical Variants

This invention also encompasses proteins or peptides having substantial amino acid sequence homology with the amino acid sequence of dendrokine. Variants include allelic and polymorphic variants, as well as species variants. In particular, various substitutions can be made, e.g., embodiments-with 10-fold substitutions, 7-fold substitutions, 5-fold substitutions, 3-fold substitutions, 2-fold, and etc. Such embodiments will typically retain particular features, e.g., antigenicity, with the natural forms.

Amino acid sequence homology, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic, polymorphic, and interspecies variations in each respective protein sequence. Typical homologous proteins or peptides will have from 25–100% homology (if gaps can be introduced), to 50–100% homology (if conservative substitutions are included) with the amino acid sequence of the dendrokine. Homology measures will be at least about 35%, generally at least 40%, more generally at least 45%, often at least 50%, more often at least 55%, typically at least 60%, more typically at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443–453; Sankoff, et al. (1983) Chapter One in *Time Warps, String Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.

The isolated dendrokine DNA can be readily modified by nucleotide substitutions, nucleotide deletions, nucleotide insertions, and short inversions of nucleotide stretches. These modifications result in novel DNA sequences which encode these antigens, their derivatives, or proteins having similar physiological, immunogenic, or antigenic activity. These modified sequences can be used to produce mutant antigens or to enhance expression. Enhanced expression may involve gene amplification, increased transcription, increased translation, and other mechanisms. Such mutant dendrokine derivatives include predetermined or site-specific mutations of the respective protein or its fragments. "Mutant dendrokine" encompasses a polypeptide otherwise falling within the homology definition of the mouse dendrokine as set forth above, but having an amino acid sequence which differs from that of dendrokine as normally found in nature, whether by way of deletion, substitution, or insertion. In particular, "site specific mutant dendrokine" generally includes proteins having significant homology with a ligand having sequences of Table 1, which share various biological activities, e.g., antigenic or immunogenic, with those sequences, and in preferred embodiments contain most of the disclosed sequences. Similar concepts apply to different dendrokine proteins, particularly those found in various warm blooded animals, e.g., mammals and birds. As stated before, it is emphasized that descriptions are generally meant to encompass all dendrokine proteins, not limited to the human embodiments provided.

Although site specific mutation sites are predetermined, mutants need not be site specific. Dendrokine mutagenesis can be conducted by making amino acid insertions or deletions. Substitutions, deletions, insertions, or combinations will be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also Sambrook, et al. (1989) and Ausubel, et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a dendrokine polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, ligand-binding or other segments may be "swapped" between different new fusion polypeptides or fragments. See, e.g., Cunningham, et al. (1989) *Science* 243:1330–1336; and O'Dowd, et al. (1988) *J. Biol. Chem,* 263:15985–15992. Thus, new chimeric polypeptides exhibiting new combinations of specificities will result from the functional linkage of ligand-binding specificities and other functional domains.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

IV. Functional Variants

The blocking of physiological response to dendrokines may result from the inhibition of binding of the ligand to its receptor, e.g., through competitive inhibition. Thus, in vitro assays of the present invention will often use isolated protein, membranes from cells expressing a recombinant membrane associated dendrokine, soluble fragments comprising receptor binding segments of these ligands, or fragments attached to solid phase substrates. These assays will also allow for the diagnostic determination of the effects of either binding segment mutations and modifications, or ligand mutations and modifications, e.g., ligand analogs.

This invention also contemplates the use of competitive drug screening assays, e.g., where neutralizing antibodies to antigen or receptor fragments compete with a test compound for binding to the protein. In this manner, the antibodies can be used to detect the presence of polypeptides which share one or more antigenic binding sites of the ligand and can also be used to occupy binding sites on the protein that might otherwise interact with a receptor.

Additionally, neutralizing antibodies against dendrokine and soluble fragments of the chemokine which contain a high affinity receptor binding site can be used to inhibit chemokine activity in tissues, e.g., tissues experiencing abnormal physiology.

"Derivatives" of dendrokine antigens include amino acid sequence mutants, glycosylation variants, and covalent or aggregate conjugates with other chemical moieties. Covalent derivatives can be prepared by linkage of functionalities to groups which are found in dendrokine amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Use of deglycosylation enzymes are also contemplated. Also embraced are versions of the same primary amino acid sequence which have other minor modifications, including phosphorylated amino acid residues, e.g., phosphotyrosine, phosphoserine, or phosphothreonine. Various crystal forms, e.g., exhibiting slower kinetics of solubilization, are provided.

A major group of derivatives are covalent conjugates of the dendrokine or fragments thereof with other proteins or polypeptides. These derivatives can be synthesized in recombinant culture such as N- or C-terminal fusions or by the use of agents known in the art for their usefulness in cross-linking proteins through reactive side groups. Preferred chemokine derivatization sites with cross-linking agents are at free amino groups, carbohydrate moieties, and cysteine residues.

Fusion polypeptides between dendrokines and other homologous or heterologous proteins, e.g., other chemokines, are also provided. Many growth factors and cytokines are homodimeric entities, and a repeat construct may have various advantages, including lessened susceptibility to proteolytic cleavage. Moreover, many receptors require dimerization to transduce a signal, and various dimeric ligands or domain repeats can be desirable. Homologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of a ligand, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, a FLAG fusion, and yeast alpha mating factor. See, e.g., Godowski, et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity tags as FLAG.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1–3, Cold Spring Harbor Laboratory. Techniques for synthesis of polypeptides are described, for example, in Merrifield (1963) *J. Amer. Chem. Soc.* 85:2149–2156; Merrifield (1986) *Science* 232: 341–347; Atherton, et al. (1989) *Solid Phase Peptide Synthesis: A Practical Approach*, IRL Press, Oxford; and Dawson, et al. (1994) *Science* 266:776–779.

This invention also contemplates the use of derivatives of dendrokines other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a dendrokine antigen can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-dendrokine antibodies or its receptor. The dendrokines can also be labeled with a detectable group, for example radio-iodinated by the chloramine T procedure, covalently bound to rare earth chelates, or conjugated to another fluorescent moiety for use in diagnostic assays. Purification of dendrokine may be effected by immobilized antibodies or receptor.

A solubilized dendrokine or fragment of this invention can be used as an immunogen for the production of antisera or antibodies specific for the ligand or fragments thereof. The purified chemokines can be used to screen monoclonal antibodies or chemokine-binding fragments prepared by immunization with various forms of impure preparations containing the protein. In particular, the term "antibodies" also encompasses antigen binding fragments of natural antibodies. Purified dendrokine can also be used as a reagent to detect antibodies generated in response to the presence of elevated levels of the protein or cell fragments containing the protein, both of which may be diagnostic of an abnormal or specific physiological or disease condition. Additionally, chemokine protein fragments may also serve as immunogens to produce antibodies of the present invention, as described immediately below. For example, this invention contemplates antibodies raised against amino acid sequences shown in Table 1, or proteins containing them. In particular, this invention contemplates antibodies having binding affinity to or being raised against specific fragments, e.g., those which are predicted to lie on the outside surfaces of protein tertiary structure.

The present invention contemplates the isolation of additional closely related species variants. Southern and Northern blot analysis should establish that similar genetic entities exist in other mammals. It is likely that dendrokines are widespread in species variants, e.g., rodents, lagomorphs, carnivores, artiodactyla, perissodactyla, and primates.

The invention also provides means to isolate a group of related chemokines displaying both distinctness and similarities in structure, expression, and function. Elucidation of many of the physiological effects of the proteins will be greatly accelerated by the isolation and characterization of distinct species variants of the ligands. In particular, the present invention provides useful probes for identifying additional homologous genetic entities in different species.

The isolated genes will allow transformation of cells lacking expression of a corresponding dendrokine, e.g., either species types or cells which lack corresponding ligands and exhibit negative background activity. Expression of transformed genes will allow isolation of antigenically pure cell lines, with defined or single specie variants. This approach will allow for more sensitive detection and discrimination of the physiological effects of dendrokine receptor proteins. Subcellular fragments, e.g., cytoplasts or membrane fragments, can be isolated and used.

Dissection of critical structural elements which effect the various differentiation functions provided by ligands is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390.

In particular, receptor binding segments can be substituted between species variants to determine what structural features are important in both receptor binding affinity and specificity, as well as signal transduction. An array of different chemokine variants will be used to screen for ligands exhibiting combined properties of interaction with different receptor species variants.

Intracellular functions would probably involve segments of the receptor which are normally accessible to the cytosol. However, ligand internalization may occur under certain circumstances, and interaction may occur between intracellular components and normal "extracellular" segments. The specific segments of interaction of dendrokine with other intracellular components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolated by affinity methods or by genetic means, e.g., complementation analysis of mutants.

Further study of the expression and control of dendrokine will be pursued. The controlling elements associated with the proteins may exhibit differential developmental, tissue specific, or other expression patterns. Upstream or downstream genetic regions, e.g., control elements, are of interest. Differential splicing of message may lead to membrane bound forms, soluble forms, and modified versions of ligand.

Structural studies of the proteins will lead to design of new ligands, particularly analogs exhibiting agonist or antagonist properties on the receptor. This can be combined with previously described screening methods to isolate ligands exhibiting desired spectra of activities.

Expression in other cell types will often result in glycosylation differences in a particular chemokine. Various species variants may exhibit distinct functions based upon structural differences other than amino acid sequence. Differential modifications may be responsible for differential function, and elucidation of the effects are now made possible.

Thus, the present invention provides important reagents related to a physiological chemokine-binding protein interaction. Although the foregoing description has focused primarily upon the human dendrokine, those of skill in the art will immediately recognize that the invention encompasses other species counterparts, e.g., mouse, rat and other mammalian species, allelic, or polymorphic variants, as well as derivatives thereof.

V. Antibodies

Antibodies can be raised to dendrokines, including species, allelic, or polymorphic variants, and fragments thereof, both in their naturally occurring forms and in their recombinant forms. Additionally, antibodies can be raised to, or bind to, dendrokines in either their active forms or in their inactive forms, or their native or denatured conformations. Anti-idiotypic antibodies are also contemplated.

Antibodies, including binding fragments and single chain versions, against predetermined fragments of the ligands can be raised by immunization of animals with conjugates of the fragments with immunogenic proteins. Monoclonal antibodies are prepared from cells secreting the desired antibody. These antibodies can be screened for binding to normal or defective dendrokines, or screened for agonistic or antagonistic activity, e.g., mediated through a receptor for dendrokine. These monoclonal antibodies will usually bind with at least a $K_D$ of about 1 mM, more usually at least about 300 $\mu$M, typically at least about 10 $\mu$M, more typically at least about 30 $\mu$M, preferably at least about 10 $\mu$M, and more preferably at least about 3 $\mu$M or better.

The antibodies, including antigen binding fragments, of this invention can have significant diagnostic or therapeutic value. They can be potent antagonists that bind to a receptor and inhibit ligand binding or inhibit the ability of a ligand to elicit a biological response. They also can be useful as non-neutralizing antibodies and can be coupled to toxins or radionuclides so that when the antibody binds to ligand, a cell expressing it, e.g., on its surface, is killed. Further, these antibodies can be conjugated to drugs or other therapeutic agents, either directly or indirectly by means of a linker, and may effect drug targeting.

The antibodies of this invention can also be useful in diagnostic applications. As capture or non-neutralizing antibodies, they can be screened for ability to bind to the chemokines without inhibiting receptor binding. As neutralizing antibodies, they can be useful in competitive binding assays. They will also be useful in detecting or quantifying dendrokine or, indirectly, receptors.

Ligand fragments may be joined to other materials, particularly polypeptides, as fused or covalently joined polypeptides to be used as immunogens. A ligand and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; and Williams, et al. (1967) *Methods in Immunology and Immunochemistry*, Vol. 1, Academic Press, New York, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Cailf. and references cited therein; Harlow and Lane (1988) *Antibodies: A Laboratory Manual*, CSH Press; Goding (1986) *Monoclonal Antibodies: Principles and Practice* (2d ed.) Academic press, New York; and particularly in Kohler and Milstein (1975) in *Nature* 256:495–497, which discusses mine method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; and Queen et al. (1989) *Proc. Nat'l. Acad. Sci.* 86:10029–10033.

The antibodies of this invention can also be used for affinity chromatography in isolating the protein. Columns can be prepared where the antibodies are linked to a solid support, e.g., particles, such as agarose, SEPHADEX, or the like, where a cell lysate may be passed through the column, the column washed, followed by increasing concentrations of a mild denaturant, whereby the purified dendrokine protein will be released. Alternatively, antibodies may be affinity purified on immobilized ligand.

The antibodies may also be used to screen expression libraries for particular expression products. Usually the antibodies used in such a procedure will be labeled with a moiety allowing easy detection of presence of antigen by antibody binding.

Antibodies raised against dendrokine will also be useful to raise anti-idiotypic antibodies. These will be useful in detecting or diagnosing various immunological conditions related to expression of the respective antigens.

VI. Nucleic Acids

The described peptide sequences and the related reagents are useful in isolating a DNA clone encoding dendrokine, e.g., from a natural source. Typically, it will be useful in isolating a gene from other primates or rodents, e.g., mouse, and similar procedures will be applied to isolate genes from other species, e.g., warm blooded animals, such as birds and mammals. Cross hybridization will allow isolation of ligand encoding genes from other species. A number of different approaches should be available to successfully isolate a suitable nucleic acid clone.

The purified protein or defined peptides are useful for generating antibodies by standard methods, as described above. Synthetic peptides or purified protein can be presented to an immune system to generate monoclonal or polyclonal antibodies. See, e.g., Coligan (1991) *Current Protocols in Immnology* Wiley/Greene; and Harlow and Lane (1989) *Antibodies: A Laboratory Manual* Cold Spring Harbor Press. Alternatively, a dendrokine receptor can be used as a specific binding reagent, and advantage can be taken of its specificity of binding, much like an antibody would be used. However, chemokine receptors are typically 7 transmembrane proteins of the G-protein linked variety, which could be sensitive to appropriate interaction with lipid or membrane.

For example, the specific binding composition could be used for screening of an expression library made from a cell line which expresses a dendrokine. The screening can be standard staining of surface expressed ligand, or by panning. Screening of intracellular expression can also be performed by various staining or immunofluorescence procedures. The binding compositions could be used to affinity purify or sort out cells expressing the ligand.

The peptide segments can also be used to predict appropriate oligonucleotides to screen a library, e.g., to isolate polymorphic or species variants. The genetic code can be used to select appropriate oligonucleotides useful as probes for sreening. See, e.g., Table 1. In combination with polymerase chain reaction (PCR) techniques, synthetic oligonucleotides will be useful in selecting correct clones from a library. Complementary sequences will also be used as probes or primers.

This invention contemplates use of isolated DNA or fragments to encode a biologically active dendrokine polypeptide. In addition, this invention covers isolated or recombinant DNA which encodes a biologically active protein or polypeptide which is capable of hybridizing under appropriate conditions with the DNA sequences described herein. Said biologically active protein or polypeptide can be an intact ligand, or fragment, and have an amino acid sequence as disclosed in Table 1. Further, this invention covers the use of isolated or recombinant DNA, or fragments thereof, which encode proteins which are homologous to a dendrokine or which was isolated using cDNA encoding a dendrokine as a probe. Homologous nucleic acids will be identified from sequences databases. The isolated DNA can have the respective regulatory sequences in the 5' and 3' flanks, e.g., promoters, enhancers, poly-A addition signals, and others. An "isolated" nucleic acid is a nucleic acid, e.g., an RNA, DNA, or a mixed polymer, which is substantially separated from other components which naturally accompany a native sequence, e.g., ribosomes, polymerases, and/or flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with an unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features, may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragments" in a nucleic acid context is a contiguous segment of at least about 17 nucleotides, generally at least about 20 nucleotides, more generally at least about 23 nucleotides, ordinarily at least about 26 nucleotides, more ordinarily at least about 29 nucleotides, often at least about 32 nucleotides, more often at least about 35 nucleotides, typically at least about 38 nucleotides, more typically at least about 41 nucleotides, usually at least about 44 nucleotides, more usually at least about 47 nucleotides, preferably at least about 50 nucleotides, more preferably at least about 53 nucleotides, and in particularly preferred embodiments will be at least about 56 or more nucleotides, e.g., 60, 65, 75, 85, 100, 120, 150, 200, 250, 300, 400, etc.

A DNA which codes for a dendrokine protein or peptide will be particularly useful to identify genes, mRNA, and cDNA species which code for related or homologous ligands, as well as DNAs which code for homologous proteins from different species. There are likely homologues in other species, including primates. Various dendrokine proteins, e.g., polymorphic variants, should be homologous and are encompassed herein. However, even proteins that have a more distant evolutionary relationship to the ligand can readily be isolated under appropriate conditions using these sequences if they are sufficiently homologous. Primate dendrokines are of particular interest.

This invention further covers recombinant DNA molecules and fragments having a DNA sequence identical to or highly homologous to the isolated DNAs set forth herein. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Embryonic Stem Cells: A Practical Approach* IRL Press, Oxford; and Rosenberg (1992) *J. Clinical Oncology* 10:180–199.

Homologous nucleic acid sequences, when compared, exhibit significant similarity. The standards for homology in nucleic acids are either measures for homology generally used in the art by sequence comparison or based upon hybridization conditions. The hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least about 56%, more generally at least about 59%, ordinarily at least about 62%, more ordinarily at least about 65%, often at least about 68%, more often at least about 71%, typically at least about 74%, more typically at least about 77%, usually at least about 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a sequence derived from Table 1 or 3. Typically, selective hybridization will occur when there is at least about 55% homology over a stretch of at least about 30 nucleotides, preferably at least about 65% over a stretch of at least about 25 nucleotides, more preferably at least about 75%, and most preferably at least about 90% over about 20 nucleotides. See, Kanehisa (1984) *Nuc. Acids Res.* 12:203–213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 400 mM, usually less than about 300 mM, more usually less than about 200 mM, typically less than about 150 mM, preferably less than about 100 mM, and more preferably less than about 60 mM, e.g., 40 or 20. However, the combination of parameters is much more important than the measure of any single parameter. See, e.g., Wetmur and Davidson (1968) *J. Mol. Biol.* 31:349–370.

Dendrokine from other mammalian species can be cloned and isolated by cross-species hybridization of closely related species. Alternatively, sequences from a data base may be recognized as having similarity. Homology may be relatively low between distantly related species, and thus hybridization of relatively closely related species is advisable. Alternatively, preparation of an antibody preparation which exhibits less species specificity may be useful in expression cloning approaches.

VII. Making Dendrokine; Mimetics

DNA which encodes the dendrokine or fragments thereof can be obtained by chemical synthesis, screening cDNA libraries, or by screening genomic libraries prepared from a wide variety of cell lines or tissue samples.

This DNA can be expressed in a wide variety of host cells for the synthesis of a full-length ligand or fragments which can in turn, for example, be used to generate polyclonal or monoclonal antibodies; for binding studies; for construction and expression of modified molecules; and for structure/function studies. Each antigen or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, or portions thereof, may be expressed as fusions with other proteins.

Expression vectors are typically self-replicating DNA or RNA constructs containing the desired antigen gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention contain DNA which encodes a dendrokine, or a fragment thereof, typically encoding a biologically active polypeptide. The DNA can be under the control of a viral promoter and can encode a selection marker. This invention further contemplates use of such expression vectors which are capable of expressing eukaryotic cDNA coding for a dendrokine in a prokaryotic or eukaryotic host, where the vector is compatible with the host and where the eukaryotic cDNA coding for the ligand is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the ligand or its fragments in various hosts using vectors that do not contain a replication origin that is recognized by the host cell. It is also possible to use vectors that cause integration of a dendrokine gene or its fragments into the host DNA by recombination, or to integrate a promoter which controls expression of an endogenous gene.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y.; and Rodriquez, et al. (1988)(eds.) *Vectors: A Survey of Molecular Cloning Vectors and Their Uses*, Buttersworth, Boston, Mass.

Transformed cells include cells, preferably mammalian, that have been transformed or transfected with dendrokine gene containing vectors constructed using recombinant DNA techniques. Transformed host cells usually express the ligand or its fragments, but for purposes of cloning, amplifying, and manipulating its DNA, do not need to express the protein. This invention further contemplates culturing transformed cells in a nutrient medium, thus permitting the protein to accumulate in the culture. The protein can be recovered, either from the culture or from the culture medium.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the dendrokines or its fragments include, but are not limited to, such vectors as those containing the lac promoter (pUC-series); trp promoter (pBR322-trp); lpp promoter (the PIN-series); lambda-pP or pR promoters (pOTS); or hybrid promoters such as ptac (pDR540). See Brosius, et al. (1988) "Expression Vectors Employing Lambda-, trp-, lac-, and lpp-derived Promoters", in Rodriguez and Denhardt (eds.) *Vectors: A Survey of Molecular Cloning Vectors and Their Uses*, Buttersworth, Boston, Chapter 10, pp. 205–236.

Lower eukaryotes, e.g., yeasts and Dictyostelium, may be transformed with dendrokine sequence containing vectors. For purposes of this invention, the most common lower eukaryotic host is the baker's yeast, Saccharomyces cerevisiae. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active dendrokine protein. In principle, any higher eukaryotic tissue culture cell line is workable, e.g., insect baculovirus expression systems, whether from an invertebrate or vertebrate source. However, mammalian cells are preferred, in that the processing, both cotranslationally and posttranslationally. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610.

It will often be desired to express a dendrokine polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the dendrokine gene may be co-transformed with one or more genes encoding mammalian or other glycosylating enzymes. Using this approach, certain mammalian glycosylation patterns will be achievable or approximated in prokaryote or other cells.

A dendrokine, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Now that the dendrokine has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; Bodanszky (1984) *The Principles of Peptide Synthesis*, Springer-Verlag, New York; and Dawson, et al. (1994) *Science* 266:776–779. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The dendrokine, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction are typically protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxy ethyl resins, phenol resins, tert-alkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149–2156. Synthetic peptide fusion technology also exists. See, e.g., Dawson, et al. (1994) *Science* 266:776–779.

The prepared ligand and fragments thereof can be isolated and purified from the reaction mixture by means of peptide separation, e.g., by extraction, precipitation, electrophoresis and various forms of chromatography, and the like. The dendrokines of this invention can be obtained in varying degrees of purity depending upon its desired use. Purification can be accomplished by use of the protein purification techniques disclosed herein or by the use of the antibodies herein described in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the ligand, or lysates or supernatants of cells producing the dendrokine as a result of DNA techniques, see below.

VIII. Uses

The present invention provides reagents which will find use in diagnostic applications as described elsewhere herein, e.g., in the general description for developmental abnormalities, or below in the description of kits for diagnosis.

This invention also provides reagents with significant therapeutic value. The dendrokine (naturally occurring or recombinant), fragments thereof and antibodies thereto, along with compounds identified as having binding affinity to dendrokine, should be useful in the treatment of conditions associated with abnormal physiology or development, including inflammatory conditions. In particular, modulation of trafficking of leukocytes is likely, but a wider tissue distribution might suggest broader biological activity, including, e.g., antiviral effects. Abnormal proliferation, regeneration, degeneration, and atrophy may be modulated by appropriate therapeutic treatment using the compositions provided herein. For example, a disease or disorder associated with abnormal expression or abnormal signaling by a dendrokine should be a likely target for an agonist or antagonist of the ligand.

Thus, the dendrokines may be administered to a site of tumor growth, thereby attracting important effector cells to the location. These cells, perhaps induced to recognize tumor antigens, may mount an immune response to limit growth of, or destroy, the tumor.

The dendrokines may also be useful as a vaccine adjuvant, thereby improving an immune response to a desired vaccine reagent. Alternatively, a dendrokine antagonist may find use in other contexts to prevent the mounting of a strong immune response. Rheumatoid arthritis is characterized by accumulation in the joints of synovial fluid, which is rich in dendritic cells. These cells are present and perhaps contribute to the inflammatory response, leading to progression of the condition. Other autoimmune conditions may be effectively treated with an antagonist, e.g., atopy, psoriasis, atopic dermatitis, asthma, etc. Finally, transplantation events may be advantageously treated to minimize the rejection response by minimizing the role of antigen presenting cells in initiating an immune response. See, e.g., Starzl, et al. (1992) *Lancet* 339:1579–1581; and Lu, et al. (1995) *Transplantation* 60:1539–1545.

Various abnormal physiological or developmental conditions are known in cell types shown to possess dendrokine mRNA by Northern blot analysis, e.g., dendritic cells. See, e.g., Berkow (ed.) *The Merck Manual of Diagnosis and Therapy*, Merck & Co., Rahway, N.J.; and Thorn, et al. *Harrison's Principles of Internal Medicine*, McGraw-Hill, N.Y. Developmental or functional abnormalities, e.g., of the immune system, cause significant medical abnormalities and conditions which may be susceptible to prevention or treatment using compositions provided herein.

Recombinant dendrokine antibodies can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or receptor or fragments thereof can be performed to identify compounds having binding affinity to dendrokine, including isolation of associated components. Subsequent biological assays can then be utilized to determine if the compound has intrinsic stimulating activity and is therefore a blocker or antagonist in that it blocks the activity of the ligand. Likewise, a compound having intrinsic stimulating activity can activate the receptor and is thus an agonist in that it simulates the activity of dendrokine. This invention further contemplates the therapeutic use of antibodies to dendrokine as antagonists. This approach should be particularly useful with other dendrokine species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

Dendrokine, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Penn.; Avis, et al. (eds.) (1993) *Pharmaceutical Dosage Forms: Parenteral Medications* Dekker, N.Y.; Lieberman, et al. (eds.) (1990) *Pharmaceutical Dosage Forms: Tablets* Dekker, N.Y.; and Lieberman, et al. (eds.) (1990) *Pharmaceutical Dosage Forms: Disperse Systems* Dekker, N.Y. The therapy of this invention, e.g., agonists or antagonist, may be combined with or used in association with other cytokines and/or chemokine agonists or antagonists, with other chemotherapeutic or chemopreventive agents, or in combination with antigen, alloantigen or other.

Both the naturally occurring and the recombinant form of the dendrokines of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate. The development of suitable assays can be greatly facilitated by the availability of large amounts of purified, soluble dendrokine as provided by this invention.

For example, antagonists can normally be found once the ligand has been structurally defined. Testing of potential ligand analogs is now possible upon the development of highly automated assay methods using physiologically responsive cells. In particular, new agonists and antagonists will be discovered by using screening techniques described herein.

Viable cells could also be used to screen for the effects of drugs on dendrokine mediated functions, e.g., second messenger levels, i.e., $Ca^{++}$; inositol phosphate pool changes (see, e.g., Berridge (1993) *Nature* 361:315–325 or Billah and Anthes (1990) *Biochem. J.* 269:281–291); cellular morphology modification responses; phosphoinositide lipid turnover; an antiviral response. and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Rational drug design may also be based upon structural studies of the molecular shapes of the dendrokine and other effectors or analogs. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York.

Purified dendrokine can be coated directly onto plates for use in the aforementioned drug screening techniques. However, non-neutralizing antibodies to these ligands can be used as capture antibodies to immobilize the respective ligand on the solid phase.

IX. Kits

This invention also contemplates use of dendrokine proteins, fragments thereof, peptides, and their fusion products in a variety of diagnostic kits and methods for detecting the presence of ligand, antibodies, or a dendrokine receptor. Typically the kit will have a compartment containing either a defined dendrokine peptide or gene segment or a reagent which recognizes one or the other, e.g., antibodies.

A kit for determining the binding affinity of a test compound to a dendrokine would typically comprise a test compound; a labeled compound, e.g., an antibody having known binding affinity for the ligand; a source of dendrokine (naturally occurring, recombinant, or synthetic); and a means for separating bound from free labeled compound, such as a solid phase for immobilizing the ligand. Once compounds are screened, those having suitable binding affinity to the ligand can be evaluated in suitable biological assays, as are well known in the art, to determine whether they act as agonists or antagonists to the receptor. The availability of recombinant dendrokine polypeptides also provide well defined standards for calibrating such assays.

A preferred kit for determining the concentration of, e.g., a dendrokine in a sample would typically comprise a labeled compound, e.g., antibody, having known binding affinity for the ligand, a source of ligand (naturally occurring, recombinant, or synthetic) and a means for separating the bound from free labeled compound, e.g., a solid phase for immobilizing the dendrokine. Compartments containing reagents, and/or instructions on use or disposal of reagents will normally be provided.

Antibodies, including antigen binding fragments, specific for the dendrokine or ligand fragments are useful in diagnostic applications to detect the presence of elevated levels of dendrokine and/or its fragments. Such diagnostic assays can employ lysates, live cells, fixed cells, immunofluorescence, cell cultures, body fluids, and further can involve the detection of antigens related to the ligand in serum, or the like. Diagnostic assays may be homogeneous (without a separation step between free reagent and antigen-ligand complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a dendrokine or to a particular fragment thereof. Similar assays have also been extensively discussed in the literature. See, e.g., Harlow and Lane (1988) *Antibodies: A Laboratory Manual*, CSH.

Anti-idiotypic antibodies may have similar use to diagnose presence of antibodies against a dendrokine, as such may be diagnostic of various abnormal states. For example, overproduction of dendrokine may result in production of various immunological reactions which may be diagnostic of abnormal physiological states, particularly in various inflammatory conditions.

Frequently, the reagents for diagnostic assays are supplied in kits, so as to optimize the sensitivity of the assay. For the subject invention, depending upon the nature of the assay, the protocol, and the label, either labeled or unlabeled antibody or labeled dendrokine is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In these assays, the ligand, test compound, dendrokine, or antibodies thereto can be labeled either directly or indirectly. Possibilities for direct labeling include label groups: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free ligand, or alternatively the bound from the free test compound. The dendrokine can be immobilized on various matrixes followed by washing. Suitable matrixes include plastic such as an ELISA plate, filters, and beads. Methods of immobilizing the dendrokine to a matrix include, without limitation, direct adhesion to plastic, use of a capture antibody, chemical coupling, and biotin-avidin. The last step in this approach involves the precipitation of ligand/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a dendrokine. These sequences can be used as probes for detecting levels of the ligand message in samples from patients suspected of having an abnormal condition, e.g., an inflammatory or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}P$. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

The broad scope of this invention is best understood with reference to the following examples, which are not intended to limit the invention to specific embodiments.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols 1–3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York; Innis, et al. (eds.)(1990) *PCR Protocols: A Guide to Methods and Applications* Academic Press, NY Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology*, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbents" in Setlow (ed.) *Genetic Engineering, Principle and Methods* 12:87–98, Plenum Press, NY; and Crowe, et al. (1992) *OIAexpress: The High Level Expression & Protein Purification System* QIAGEN, Inc., Chatsworth, Calif.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Generation of Dendritic Cells

Human CD34+ peripheral cells are obtained. Cells were cultured in the presence of Stem Cell Factor (SCF), GM-CSF, and TNF-β in endotoxin free RPMI 1640 medium (GIBCO, Grand Island, N.Y.) supplemented with 10% (v/v) heat-inactivated fetal bovine serum (FBS; Flow Laboratories, Irvine, Calif.), 10 mM HEPES, 2 mM L-glutamine, $5\times10^{-5}$ M 2-mercaptoethanol, penicillin (100 μg/ml). This is referred to as complete medium.

CD34+ cells were seeded for expansion in 25 to 75 cm$^2$ flasks (Corning, N.Y.) at $2\times10^4$ cells/ml. Optimal conditions were maintained by splitting these cultures at day 5 and 10 with medium containing fresh GM-CSF and TNF-α (cell concentration: 1–3 $\times10^5$ cells/ml). Cells were routinely collected after 12 days of culture, eventually adherent cells were recovered using a 5 mM EDTA solution.

Cells were activated by resuspension in complete medium at $5\times10^6$ cells/ml and activated for the appropriate time (e.g., 1 or 6 h) with 1, μg/ml phorbol 12-myristate 13-acetate (PMA, Sigma) and 100 ng/ml ionomycin (Calbiochem, La Jolla, Calif.).

III. RNA Isolation and Library Construction

Total RNA is isolated using the guanidine thiocyanate/CsCl gradient procedure as described by Chirgwin, et al. (1978) *Biochem.* 18:5294–5299.

Alternatively, poly(A)+RNA is isolated using the OLIGOTEX mRNA isolation kit (QIAGEN). Double stranded cDNA are generated using the SUPERSCRIPT plasmid system (Gibco BRL, Gaithersburg, Md.) for cDNA synthesis and plasmid cloning. The resulting double stranded cDNA is unidirectionally cloned into pSport1 and transfected by electroporation into ELECTROMAX DH10B™ Cells (Gibco BRL, Gaithersburg, Md.).

IV. Sequencing

DNA isolated from randomly picked clones were subjected to nucleotide sequence analysis using standard techniques. A Taq DiDeoxy Terminator cycle sequencing kit (Applied Biosystems, Foster City, Calif.) can be used. The labeled DNA fragments can be separated using a DNA sequencing gel of an appropriate automated sequencer. Alternatively, the isolated clone is sequenced as described, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols 1–3, CSH Press, NY; Ausubel, et al., *Biology*, Greene Publishing Associates, Brooklyn, N.Y.; or Ausubel, et al. (1987 and Supplements)

*Current Protocols in Molecular Biology*, Greene/Wiley, New York. Chemical sequencing methods are also available, e.g., using Maxam and Gilbert sequencing techniques.

Dendrokine was originally isolated from a library constructed from PMA-ionomycin activated dendritic cells generated in vitro by culturing CD34+ hematopoietic progenitor cells in the presence of GM-CSF and TNF-α. See Caux, et al. (1992) *Nature* 360:258–261. The sequence of dendrokine is determined using primers corresponding to several overlapping fragments, in both directions. Related sequences may be identified from, e.g., various gene sequence databases such as GenBank.

V. Distribution of Dendrokine

Total RNA/poly(A)+ RNA is separated on a 1% denaturing agarose gel and blotted onto a HYBOND-N+ membrane (Amersham, Arlington Heights, Ill.). Subsequently, the northern blot is hybridized with a $^{32}$p-end-labeled oligo specific for the newly identified chemokine.

Dendrokine expression was detected in cultured activated dendritic cells. It was not detected in activated cell lines: TF1, Jurkat T cells, CHA carcinoma cells, MRC5 lung fibroblast cells, JY EBV transformed cells, or U937 promonocytic cells. Among tissues, a multiple human tissue blot from Clontech (cat 7759-1), the message was not detected in spleen, prostate, testis, ovary, small intestine, colon, or PBL, but a very faint signal was detected in thymus, possibly due to dendritic cells therein.

Alternatively, the binding compositions are used to affinity purify or sort out cells expressing the ligand. See, e.g., Sambrook, et al. or Ausubel et al. Immunohistology may also determine cell types expressing the protein. Distribution data may be derived from sequence databases, e.g., identification of cell or tissue sources which contain message encoding the sequence.

VI. Amino Terminal Mapping

In order to obtain material for peptide mapping, PCR is performed using a 5' primer corresponding the pSport1 cDNA vector (Gibco BRL, Gaithersburg, Md.) which is 5' to the dendrokine insert, as well as 3' primer that hybridizes to the C-terminal coding region. The 3' primer also incorporates a FLAG-tag sequence (Eastman Kodak, Haven, Conn.) and a stop codon. The resulting PCR fragment is cloned into pME18S, transfected into COS cells, and transiently expressed. Supernatant is collected over several days, and affinity purified over an M2 column (Eastman Kodak, New Haven, Conn.). The eluted protein is sequenced and the N-terminus of the mature secreted protein defined. See Table 1.

VII. Purification of Dendrokine

With a clone encoding a dendrokine chemokine, recombinant production means are used, although natural forms may be purified from appropriate sources. The protein product is purified by standard methods of protein purification, in certain cases, e.g., coupled with immunoaffinity methods. Immunoaffinity methods are used either as a purification step, as described above, or as a detection assay to determine the separation properties of the protein.

Preferably, the protein is secreted into the medium, and the soluble product is purified from the medium in a soluble form. Alternatively, inclusion bodies from prokaryotic expression systems are a useful source of material. Typically, the insoluble protein is solubilized from the inclusion bodies and refolded using standard methods. Purification methods are developed as described above.

Preferably, the protein is made in a eukaryotic cell which glycosylates the protein normally. The purification methods may be affected thereby, as may biological activities.

VIII. Preparation of Antibodies Against Dendrokine

Using purified dendrokine protein, animals are immunized to produce antibodies. Polyclonal antiserum is raised using non-purified antigen, though the resulting serum will exhibit higher background levels. Preferably, the antigen is purified using standard protein purification techniques, including, e.g., affinity chromatography using polyclonal serum indicated above. Presence of specific antibodies is detected using defined synthetic peptide fragments.

Polyclonal serum is raised against a purified antigen, purified as indicated above, or using synthetic peptides. A series of overlapping synthetic peptides which encompass all of the full length sequence, if presented to an animal, will produce serum recognizing most linear epitopes on the protein. Such an antiserum is used to affinity purify protein, which is, in turn, used to introduce intact full length protein into another animal to produce another antiserum preparation.

Similar techniques are used to generate induce monoclonal antibodies to either unpurified antigen, or, preferably, purified antigen.

IX. Biological Activities, Direct and Indirect

A robust and sensitive assay is selected, e.g., on hematopoietic cells. Chemokine is added to the assay in increasing doses to see if a dose response is detected. For example, in a proliferation assay, cells are plated out in plates. Appropriate culture medium is provided, and chemokine is added to the cells in varying amounts. Growth is monitored over a period of time which will detect either a direct effect on the cells, or an indirect effect of the chemokine.

Alternatively, an activation assay or attraction assay is used. An appropriate cell type is selected, e.g., hematopoietic cells, myeloid (macrophages, neutrophils, polymorphonuclear cells, etc.) or lymphoid (T cell, B cell, or NK cells), neural cells (neurons, neuroglia, oligodendrocytes, astrocytes, etc.), or stem cells, e.g., progenitor cells which differentiate to other cell types, e.g., gut crypt cells and undifferentiated cell types.

Other assays will be those which have been demonstrated with other chemokines. See, e.g., Schall and Bacon (1994) *Current Opinion in Immunology* 6:865–873; and Bacon and Schall (1996) *Int. Arch. Allergy & Immunol.* 109:97–109.

X. Structure Activity Relationship

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity. Studies may be performed making, e.g., muteins with few variations, or with specific combinations of mutations.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population distributions, etc.

All references cited herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of the equivalents to which such claims are entitled.

What is claimed is:

1. An isolated polynucleotide comprising the nucleic acid sequence of SEQ ID NO: 1.

2. An expression vector comprising the polynucleotide of claim 1.

3. A host cell comprising the vector of claim 2.

4. A method for producing a polypeptide comprising culturing the host cell of claim 3 under conditions in which the polypeptide is expressed, and recovering said polypeptide.

5. An isolated polynucleotide encoding a polypeptide comprising the amino acid sequence of SEQ ID NO: 2.

6. The polynucleotide of claim 5 comprising nucleotides 1–330 of SEQ ID NO: 1.

7. An expression vector comprising the polynucleotide of claim 5.

8. A host cell comprising the vector of claim 7.

9. A method for producing a polypeptide comprising culturing the host cell of claim 8 under conditions in which the polypeptide is expressed, and recovering said polypeptide.

* * * * *

UNITED STATES PATENT AND TRADEMARK OFFICE
CERTIFICATE OF CORRECTION

PATENT NO.    : 6,812,004 B1
DATED         : November 2, 2004
INVENTOR(S)   : Caux et al.

It is certified that error appears in the above-identified patent and that said Letters Patent is hereby corrected as shown below:

<u>Title page,</u>
Item [*] Notice, delete "639" and substitute therefore -- 61 --.

Signed and Sealed this

Eighth Day of February, 2005

JON W. DUDAS
*Director of the United States Patent and Trademark Office*